United States Patent [19]
Velde et al.

[11] Patent Number: 4,778,447
[45] Date of Patent: Oct. 18, 1988

[54] CONNECTORS

[75] Inventors: Christian V. Velde, Uccle; Patrick Balteau, Saint-Georges-Sur-Meuse, both of Belgium

[73] Assignee: Travenol European Research & Development Center, Brussels, Belgium

[21] Appl. No.: 496,766

[22] Filed: May 20, 1983

[51] Int. Cl.⁴ .............................................. A61M 5/00
[52] U.S. Cl. ...................................... 604/29; 604/283; 604/905
[58] Field of Search .......................... 604/29, 283, 905

[56] References Cited

U.S. PATENT DOCUMENTS 4,294,250 10/1981 Dennehey .
4,349,024 9/1982 Ralston, Jr. ......................... 604/905
4,354,490 10/1982 Rogers .
4,417,890 11/1983 Dennehey et al. ................. 604/905
4,432,764 2/1984 Lopez ................................. 604/283
4,457,749 7/1984 Bellotti et al. ...................... 604/905

FOREIGN PATENT DOCUMENTS 994631 10/1976 Canada .
2853635 6/1980 Fed. Rep. of Germany .

Primary Examiner—C. Fred Rosenbaum
Assistant Examiner—Frank Wilkens
Attorney, Agent, or Firm—Paul C. Flattery; Daniel D. Ryan; Charles R. Mattenson

[57] ABSTRACT

Connector devices residing on the ends of conduits or lines and intended to connect conduits or lines in flow relation are the subject matter of this invention. Caps for capping the connectors to isolate the open ends of the connectors and close them when desired are also taught herein. Caps and connectors disclosed by this invention are suited for use as medical connectors and caps.

16 Claims, 3 Drawing Sheets

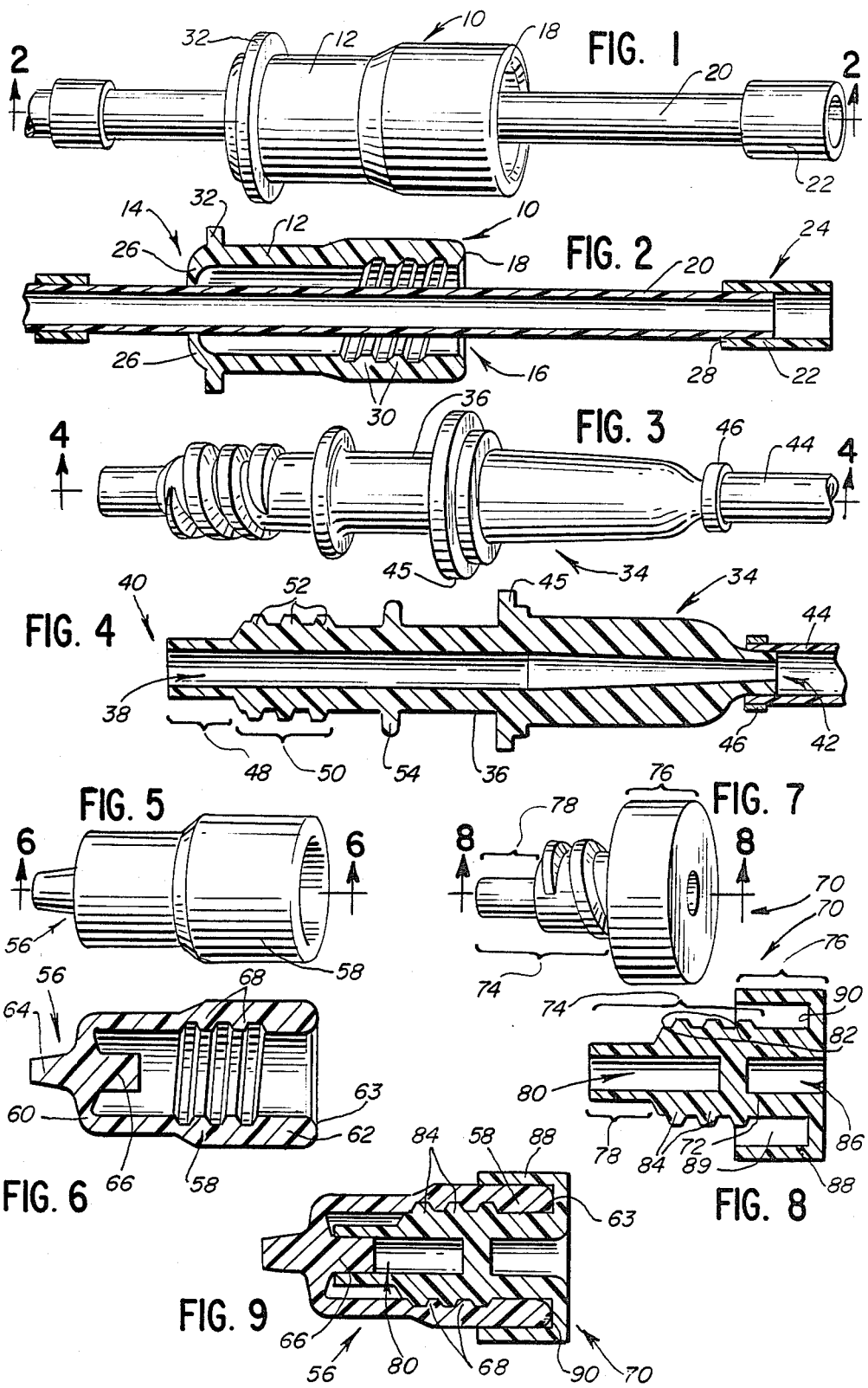

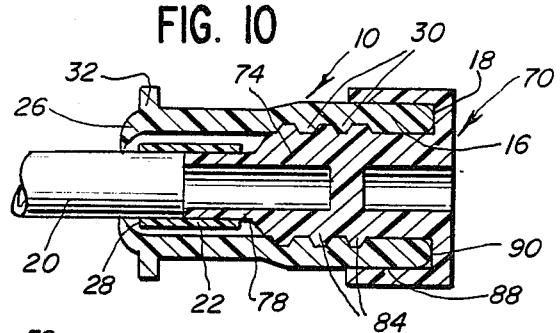
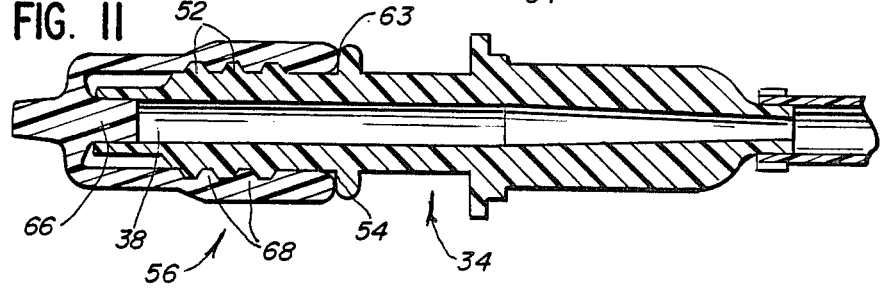
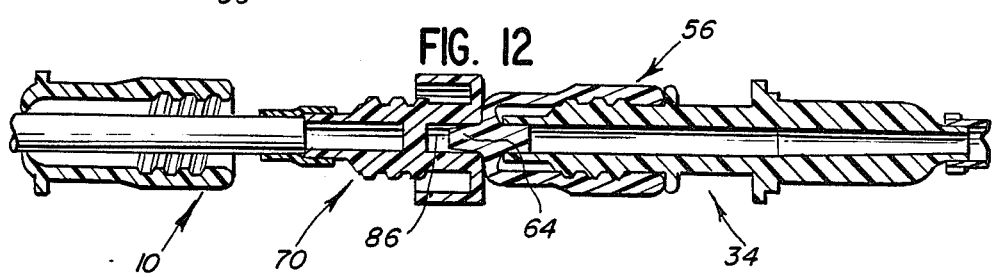
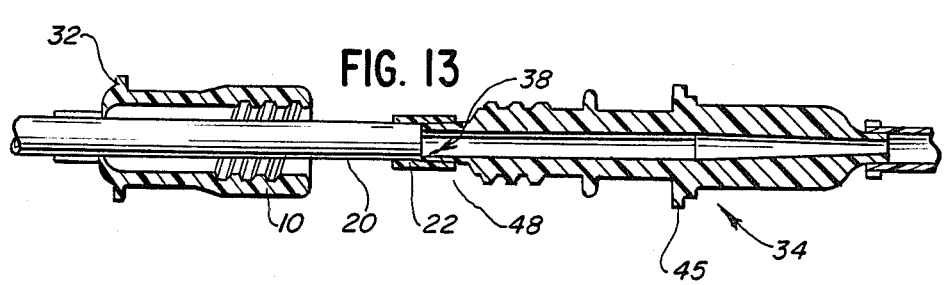
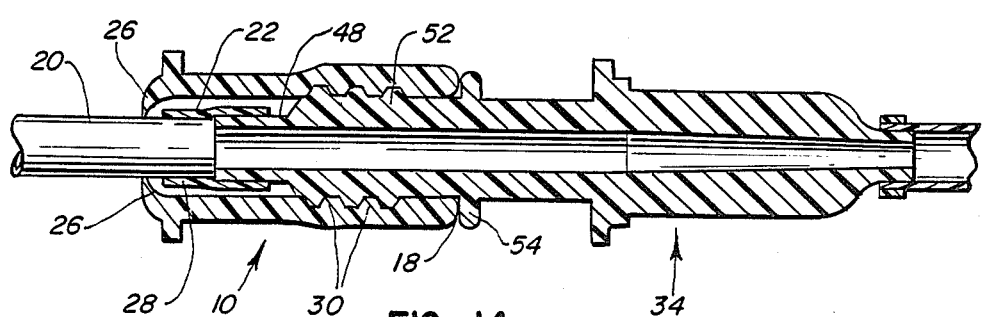

CONNECTORS

FIELD OF THE INVENTION

This invention relates to connectors residing on the ends of conduits or lines and intended to connect these conduits or lines in flow relation. This invention also relates to caps to close and isolate the open ends of the connectors. The particular province of this invention resides in connectors for connecting medical fluid lines in flow relation, preferably in an antiseptic manner. Caps for the connectors are also part of this invention and are particularly suited for capping the ends of the medical connectors and preferably maintaining them in an antiseptic state when the ends of the connectors are to remain closed. When not in use, each cap can be used to close the other, thereby minimizing contamination of the cap interiors during storage.

BACKGROUND OF THE INVENTION

Typical medical connectors in wide use are connectors for solution containers, administration sets, catheters and numerous medical lines. Medical procedures require a connection where the bio-burden (i.e., bacterial population) is minimized. Protective caps containing an antibacterial agent or connectors and caps susceptible to ultraviolet radiation disinfection can result in reduced bio-burden by providing a bacteriocidal or bacteriostatic effect to connector surfaces and to cap surfaces prior to use. Sterile or antiseptic surfaces on connectors and caps are desirable particularly for lines, connectors and components used in peritoneal dialysis, for example, continuous ambulatory peritoneal dialysis (CAPD).

At the present time thousands of patients who have limited or nonexistent kidney function due to end stage renal disease are being maintained by CAPD and other forms of peritoneal dialysis. In the CAPD procedure, connections between dialysis solution containers and administration sets which communicate with the peritoneal catheter must be made and broken, normally several times a day. There is the possibility that sterility of the flow path between the various solution containers and the peritoneal cavity may be compromised, particularly when the patient is doing his own CAPD exchanges. Airborne bacteria or accidental touch contamination of an open connector by the patient can contaminate the flow path. The result of such a contamination can be peritonitis.

It would be expedient to provide connectors which safely seal at connector sites without the rigidly enforced molding tolerances which are presently necessary.

It would be desirable if opportunities for accidental disconnection of the tubing conduits were prevented or minimized.

It would be favorable if reduced bio-burden around the connection site were promoted by the connector design.

It would be advantageous if connectors provided a smooth fluid flow path without obstruction and without steps or abrupt changes in lumen cross-section.

A favorable construction would have good sealing characteristics achievable with minimum forces required to operate the connection.

An effective bacteriostatic or bacteriocidal connection system could be made of a material that did not support bacteria growth, yet which is transparent to ultraviolet radiation for disinfecting or preferably sterilizing the connection surfaces before use.

BRIEF SUMMARY OF THE INVENTION

Novel connectors for connecting fluid flow lines in flow relation, caps for capping the connectors and themselves fitting together in various configurations are the subject of the present invention. The connector system essentially comprises a female connector, a mating male connector, a male cap for fitting on the female connector and a female cap for capping the male connector. Additionally, the male and female caps may be fitted together in a number of configurations. Typically, the caps are assembled and fitted to each other in one configuration for storage and in another configuration when they close their respective connectors and fix them for radiation disinfection.

The female connector of the present invention is adapted to be carried along a conduit or medical tubing line. A sleeve fits over the connector end or terminal end of the conduit or line. Additionally, a second sleeve may be located further back from the connector end along the outside of the conduit or line. The female connector is located between the two sleeves with the second sleeve functioning as a retention ring.

The female connector comprises an elongated sheath having open first and second ends, and it is adapted to be slidably carried along the medical line or conduit. The first open end of the female connector terminates in an inwardly directed lip which sealingly abuts, at the connector or sheath interior, with the terminal sleeve on the conduit. An interior surface of the sheath at the second open end has a threaded portion for mating with a mating externally threaded device. Normally having a circular cross-sectional configuration, the female connector additionally can have an outwardly directed ferrule at the first open end which stiffens the first open end and promotes a more secure abutting, sealing engagement between the lip on the first open end and the terminal sleeve on the conduit or line.

Indeed, the ferrule also is designed to fit in the alignment channels of a conventionally available ultraviolet disinfection device, U.S. patent application Pat. No. 4,433,244, "*Apparatus for Irradiating Tubing Connections*", to Hogan, issued Feb. 21, 1984 [hereinafter cited as Hogan] assigned to Baxter Travenol Laboratories, Inc. Preferably, the female connector is made from low density polyethylene (LDPE) thermoplastic material. The female connector is carried on an extension line made of silicone rubber having a sleeve also made from silicone rubber.

The male connector of this invention generally comprises an elongated member having an axial bore therethrough. The axial bore extends from a first open end to a second open end. The bore diameter at the first open end is essentially the same as the conduit bore it connects to. The first open end has a forward portion and a rearward portion. The forward portion is adapted for telescoping engagement with a conduit, for example, the sleeve on the terminal end of the medical fluid line described above. The rearward portion on the first end is externally threaded for engaging an internally threaded, mating portion on a connector, cap or the like. A flange, behind the rearward portion on the first end sealingly abuts the periphery on the open end of a mating female connector, female cap or the like. The first end stops at an outwardly directed ferrule designed to fit in the alignment channels of the Hogan device.

The forward portion of the first end of the male connector telescopically engages the sleeve on the terminal end of another connector or line, for example, the sleeved conduit used with the female connector. The conduit bore essentially is the same diameter as the male connector bore allowing a smooth transition from connector to conduit. A smooth fluid flow path is provided without abrupt changes or steps in lumen or bore cross-section.

Then, the female connector engages the male connector at the threaded portion. When the female connector is threaded onto the male connector, the periphery of the open second end of the female connector sealingly abuts the flange on the male connector. Another seal is provided where the inwardly directed lip on the first end of the female connector engages the end of the sleeve on the conduit. A primary seal, of course, is provided because of the telescoping engagement of the forward portion on the first end of the male connector and the sleeve on the line or conduit.

Excellent sealing characteristics of this invention are thus achieved with only minimal forces required to operate the connection. This design minimizes the opportunities for accidental disconnection, and molding tolerances can be less rigid when the sleeve on the extension line is made from silicone rubber. The silicone rubber sleeve is elastic enough to deform and thereby compensate for slight variations in the size of the forward portion on male connectors.

Desirably, the male connector is made of poly(4-methyl-1-pentene) material, such as TPX ™ thermoplastic manufactured by Mitsui Chemical Co. (TPX ™ is a trademark of Mitsui Chemical Co.) when multiple use is desired. Polyolefin thermoplastic materials are materials of choice when single use of the male connector is desired.

Male and female caps are also part of the connector system of the present invention. The male cap is adapted for capping the open end of the female connector and it is designed to engage the female cap.

The male cap is adapted for capping the open end of a female connector, a female cap or the like. The male cap generally comprises an elongated member having cap first and second ends. The cap first end has a forward portion for telescopically engaging a conduit or a line. A rearward portion on the cap first end has external threads for mating cooperation with internal threads of a female connector, a female cap or the like. The cap first end also may have an axial bore therein for receiving a projecting lug or the like in telescoping relationship. The cap second end also may have an axial bore therein for receiving a mating projection in telescoping relationship. Preferred materials for the male cap are TPX ™ thermoplastic and polypropylene, or other appropriate ultraviolet-transparent materials.

The female cap of the present invention is adapted for placement on a male connector or for receiving a male cap or the like. The female cap comprises an elongated sheath having cap first and second ends with the cap first end being closed. Cap first end has an outwardly directed lug thereon for being received in a mating bore or aperture. The cap second end has an internally threaded portion for cooperating with mating externally threaded portions on a male connector or a male cap or the like. The extreme interior of the female connector may have an absorbent type of material therein for retaining an antiseptic solution. The extreme interior end of the cap alternatively may have a projecting portion for telescopically engaging a bore on a male connector or a male cap. A preferred material for the female cap is a LDPE thermoplastic.

In an embodiment of this invention, the male cap engages the conduit having the female connector thereon. The forward portion of the male cap first end telescopically fits in the sleeve of the conduit. The internal threaded portion of the female connector may then engage the external threaded portion on the male cap. The inwardly extending lip on the first end of the female connector then engages the sleeve while the periphery of the female connector second end abuts the second end of the male cap.

The female cap then fits over the male connector with the internal threaded portion of the cap engaging the external threaded portion on the connector and the periphery of the second end in sealing abutment with the projecting flange on the male connector. The outwardly projecting lug on the first end of the female cap may then fit in the axial bore in the second end of the male cap. Several arrangements allow the capped-connector system and the joined connector system to be placed in conventionally available ultraviolet disinfection devices, for example, the device of the Hogan application. With the male connector capped and screwed closed, with the male cap engaging the conduit terminal sleeve, and with the caps joined, the ferrules on the male and female connectors can be fitted into alignment grooves on ultraviolet disinfection devices. Similarly, with the forward portion of the male connector in telescoping engagement with the terminal sleeve on the conduit, placement in an ultraviolet disinfection device can be accomplished.

Of course, the connectors and caps of the present invention can be disinfected using conventionally available disinfectant wrapping systems. Connection sites can be covered by absorbent material or sponges soaked in povidone iodine or the like. Indeed, the caps and connectors can be made from materials that have been compounded with disinfecting agents for continuous release of these agents to provide bactericidal effect at connection sites.

A benefit of the present invention is a connector system which safely seals between a telescoping conduit connection and the connector connection where molding tolerances need not be rigidly enforced. The female connector portion of the present invention acts as a locking slide shield which prevents accidental disconnection of the tubing conduit and the male connector and provides additional sealing at the site of the abutting sealing engagement of the conduit sleeve and the inwardly directed lip on the female connector.

Another benefit of the present invention is its convenient use with presently available ultraviolet disinfection devices. Furthermore, the slide shield configuration of the female connector isolates the male connector and the conduit which reduces the bio-burden at the connection site.

Further benefit in the present invention resides in the relatively smooth connection at the conduit sleeve and male connector. Abrupt changes in lumen cross-section are eliminated which reduces potential fibrin entrapment problems during drainage of spent dialysis solution.

Further benefits achievable with this invention are the bacteriostatic or bacteriocidal characteristics of the connection system when the conduit and sleeve are made from a material that does not support bacteria growth by its nature, or because it has been treated with a disinfecting agent that is released continuously.

Other benefits and advantages of this invention will become apparent upon reading the following detailed description and appended claims.

BRIEF DESCRIPTION OF THE DRAWINGS

For a more complete understanding of this invention, reference should now be had to the embodiments illustrated in greater detail in the accompanying drawings.

In the drawings:

FIG. 1 is a perspective view illustrating the female connector of the present invention carried on a conduit which has a sleeve at its terminal, connector end.

FIG. 2 is a view taken at 2—2 in FIG. 1 showing the female connector and conduit in cross-section.

FIG. 3 is a perspective view of the male connector of the present invention.

FIG. 4 illustrates in cross-section, taken at 4—4 in FIG. 3, the male connector of the present invention.

FIG. 5 illustrates, in perspective, the female cap of the present invention.

FIG. 6 illustrates a cross-sectional view taken at 6—6 in FIG. 5 of the female cap of the present invention.

FIG. 7 is a perspective view of the male cap of the present invention.

FIG. 8 is a cross-sectional view taken at 8—8 in FIG. 7 showing the male cap of the present invention.

FIG. 9 illustrates, in cross-section, the sealing, mating relationship of the female and male caps of the present invention.

FIG. 10 illustrates, in cross-section, the female connector of the present invention capped with the male cap.

FIG. 11 illustrates, in cross-section, the male connector of the present invention capped by the female cap.

FIG. 12 is a cross-sectional view showing the capped female and male connectors with the male and female caps in engaging arrangement.

FIG. 13 illustrates the male connector engaging the sleeve of the conduit on which the female connector resides.

FIG. 14 illustrates, in cross-section, the connected, sealed male and female connectors of the present invention.

DESCRIPTION OF THE PREFERRED EMBODIMENTS

Figure 15:
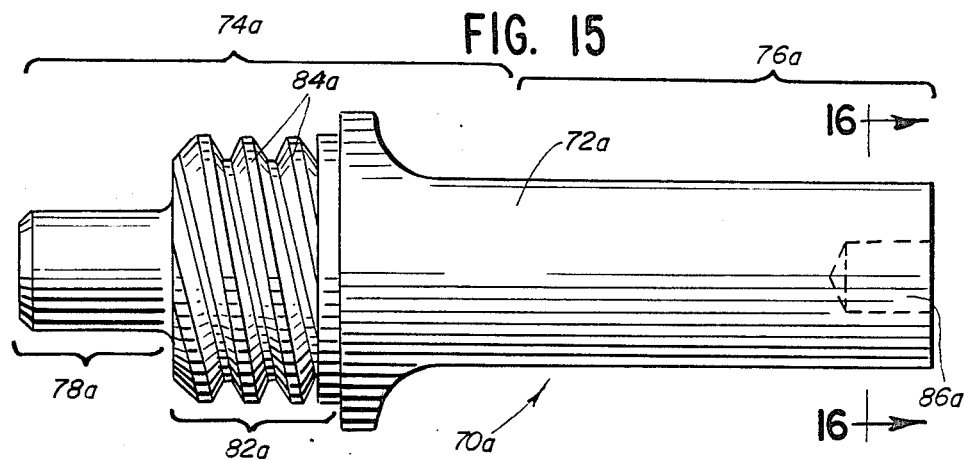
FIG. 15 is a plan view of another embodiment of the male cap of the present invention.

Turning now to the drawings, FIG. 1 illustrates female connector 10 of the present invention. Connector 10 generally comprises elongated outer sheath 12. As is shown in FIG. 2, connector 10 has open first end 14 and open second end 16. Second end 16 has periphery 18. Open ends 14, 16 allow connector 10 to be slidably carried along conduit 20. Conduit 20 has sleeve 22 in telescoping relationship at its connector end 24.

First open end 14 on sheath 12 terminates in inwardly directed lip 26. Inwardly directed lip 26 is adapted for abutting, sealing engagement at the interior of sheath 12 with end 28 on sleeve 22. Second open end 16 of sheath 12 has internal threads 30 for cooperating with mating external threads.

The axial cross-sectional configuration of sheath 12 is preferably circular. Additionally, first end 14 of sheath 12 may have an outwardly directed ferrule 32 which provides stiffness at first open end 14, thus enhancing abutting, sealing engagement of inwardly directed lip 26 with end 28 of conduit 20. Also, ferrule 32 fits in an alignment channel on some available ultraviolet disinfection devices.

Male connector 34 is illustrated in FIGS. 3 and 4. Male connector 34 is generally an elongated member 36 having axial bore 38 therethrough. Male connector 34 has first end 40 and second end 42. Second end 42 has conduit 44 telescoping thereover with compression ring 46 providing sealing engagement. Ferrule 45 can fit into an alignment channel on certain ultraviolet disinfection devices.

First end 40 defines forward portion 48 and rearward portion 50. Forward portion 48 is designed for telescoping engagement with a conduit, a mating connector, a mating cap or the like. Rearward portion 50 of first end 40 has external threads 52 for mating engagement with internal threads on a connector, a cap or the like. Rearward of second portion 50 is flange 54 designed for sealingly abutting with the outer periphery of a mating connector, a mating cap or the like, for example, periphery 18 on second end 16 of female connector 10. Male connector 34 preferably has a circular axial cross-section.

Turning now to FIGS. 13 and 14, the connector system of the present invention comprised of female connector 10, male connector 34, conduit 20 and sleeve 22 is shown. Forward portion 48 of first end 40 on male connector 34 telescopically engages sleeve 22 on conduit 20. External threads 52 on male connector 34 engage internal threads 30 on female connector 10 as is shown in FIG. 14. Seals of the connection are provided at the following locations: the mating of internal threads 30 and external threads 52; the telescoping surfaces of forward portion 48 and sleeve 22; periphery 18 of female connector 10 and flange 54 of male connector 34; and, inwardly directed lip 26 of female connector 10 and end 28 of sleeve 22. A principal seal is the seal provided at the telescoping surfaces of forward portion 48 and sleeve 22.

FIG. 13 illustrates the partially closed condition of the connector system. In this condition the connector system can be placed in the Hogan device for ultraviolet disinfection. Ferrule 45 on male connector 34 and ferrule 32 on female connector 10 can be placed in alignment channels of the Hogan device. Thereafter, connectors 34, 10 and line 20 can be disinfected.

FIGS. 5 and 6 illustrate female cap 56 of the present invention. Female cap 56 generally comprises an elongated sheath 58 having cap first end 60 and cap second end 62. Cap first end 60 is closed and has lug 64 directed from the exterior and designed to be received in a mating aperture or bore. Cap first end 60 additionally may have lug 66 directed into the interior of sheath 58. Lug 66 is designed telescopically to engage a bore or mating aperture. Second end 62 of female cap 56 has an internal threaded portion comprised of threads 68. Threads 68 are designed to mate with an externally threaded portion on a male connector, a male cap or the like, for example, male connector 34. Also, second end 62 has periphery 63 which can sealingly abut a contacting flange, flat surface or the like.

FIGS. 7 and 8 show male cap 70. Male cap 70 generally comprises an elongated portion 72. Male cap 70 defines cap first end 74 and cap second end 76. Cap first end 74 has forward portion 78 for telescopically engaging a conduit or other aperture. Cap first end 74 is shown with an axial bore 80 therein. Rearward portion 82 of cap first end 74 has external threads 84 for engaging internal threads on a cooperating female connector, female cap or the like.

Cap second end 76 of male cap 70 has axial bore 86 therein. Axial bore 86 can receive a mating lug, for example, lug 64 of female cap 56. Collar means 88 are also shown on male cap 70. Collar means 88 are adapted to envelop a portion of an engaged mating device. Surface 90 sealingly abuts periphery 18 on female connector 10, periphery 63 on female cap 56 or the like. Also, an absorbent material containing an antiseptic can be placed in channel 89 between collar 88 and elongated portion 72.

Female cap 56 and male cap 70 are shown in engaging relationship in FIG. 9. Lug 66 telescopically engages axial bore 80 of male cap 70. External threads 84 on male cap 70 engage internal threads 68 on female cap 56. Periphery 63 sealingly abuts surface 90 of male cap 70. Collar 88 of male cap 70 envelops female cap second end 62.

Figure 16:
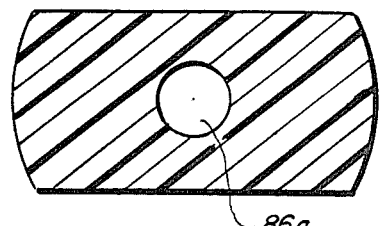
FIG. 16 is a cross-section taken at 16—16 in FIG. 15 which shows the general cross-sectional configuration of a portion of the cap.

FIGS. 15 through 18 illustrate additional embodiments of male cap 70 and female cap 56. Male cap 70a is shown in FIG. 15. This embodiment of male cap 70a is substantially similar to male cap 70 depicted in FIGS. 8 and 9 except as otherwise described herein. Male cap 70a has a generally elongated member 72a which defines cap first end 74a and cap second end 76a. Cap first end 74a has forward portion 78a and rearward portion 82a. Forward portion 78a is designed to telescopically engage a mating bore, conduit or aperture on a mating connector or the like. Rearward portion 82a has external threads 84a for cooperating with mating internal threads on a connector, a cap or the like. Second end 76a of male cap 70a has axial bore 86a therein. Bore 86a is designed to receive a mating lug or the like. FIG. 16 illustrates the cross-sectional configuration of cap second end 76a.

Figure 17:
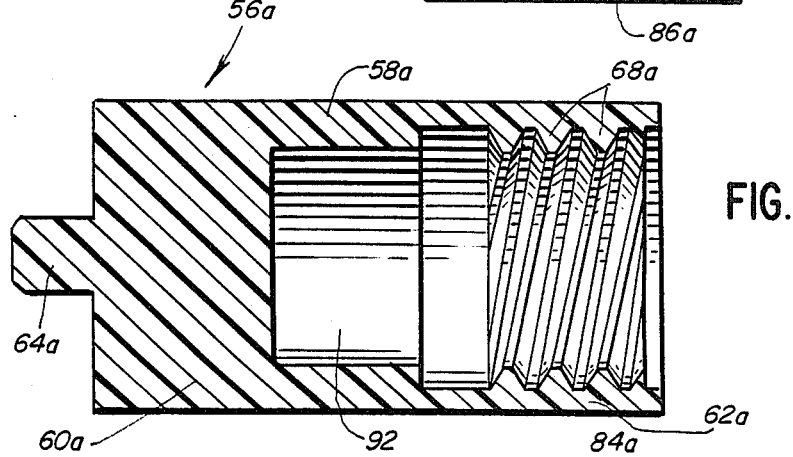
FIG. 17 illustrates, in cross-section, another embodiment of the female cap of the present invention.

FIG. 17 illustrates another embodiment of female cap 56. Female cap 56a is substantially similar to female cap 56 depicted in FIGS. 5 and 6 except as otherwise described herein. Female cap 56a generally comprises an elongated sheath 58a having cap first end 60a and cap second end 62a. Cap first end 60a is closed and has lug 64a directed from the exterior and designed to be received in a mating aperture or bore. Cap second end 62a of female cap 56a has an internal threaded portion comprised of threads 68a. Threads 68a are adapted to engage cooperating, externally threaded devices such as caps, connectors or the like. Female cap 56a also has an inner chamber 92. Inner chamber 92 can be used to receive a member projecting thereinto and can be used to retain antiseptic.

Figure 18:
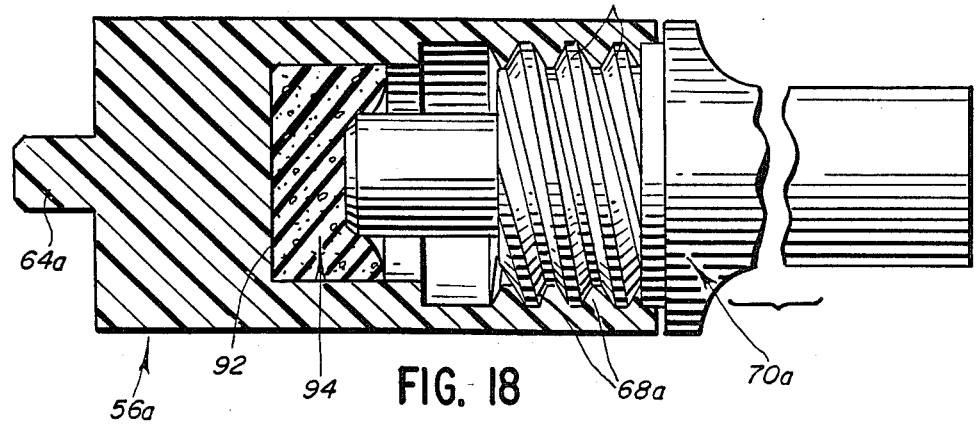
FIG. 18 is a sectional view showing the male and female caps of the present invention in engaging relationship.

FIG. 18 illustrates male cap 70a and female cap 56a in mating communication. External threads 84a on male cap 70a engage internal threads 68a on female cap 56a. Absorbent material 94, containing an antiseptic, is retained in inner chamber 92 thereby providing an antiseptic environment for the connected male and female caps.

Female connector 10 is shown capped by male cap 70 in FIG. 10. Sleeve 22 on conduit 20 is shown in telescoping relationship with forward portion 78 of the first end 74 of male cap 70. Internal threads 30 of female connector 10 engage external threads 84 of male cap 70. Outer periphery 18 of female connector second end 16 contacts surface 90 of cap 70 and is in abutting, sealing engagement. Collar 88 envelops a portion of female connector second end 16. Inwardly directed lip 26 on female connector 10 sealingly abuts against sleeve end 28. In this manner, female connector 10 can be capped, thereby minimizing compromises to the sterility of the connector.

FIG. 11 shows male connector 34 being capped by female cap 56. Periphery 63 of female cap 56 is in abutting engagement with flange 54 on male connector 34. External threads 52 on connector 34 engage internal threads 68 on female cap 56. Lug 66 on female cap 56 is in telescoping relationship with axial bore 38 of male connector 34. By capping male connector 34, compromises to sterility can be minimized.

FIG. 12 illustrates capped male connector 34 and female connector 10 just prior to completion of the capping. When female connector 10 engages male cap 70 (as illustrated in FIG. 10), lug 64 on female cap 56 engages axial bore 86 of male cap 70. Capping and connection as illustrated in FIG. 12 allows the entire structure to be inserted into conventionally available ultraviolet light sterilizing equipment for sterilization of caps and connectors prior to use.

The above has been offered for illustrative purposes, and is not intended to limit the invention of this application, which is defined in the claims below.

What is claimed is:

1. In combination with a medical conduit terminating in a sleeve attached to the conduit, the sleeve having an end face, a female connector adapted to be carried along the conduit comprising:
   an elongated outer sheath having open first and second ends and defining an exterior and an interior, said open ends enabling said sheath to be slidably carried along the conduit:
   said first open end terminating in an inwardly directed lip adapted for abutting sealing engagement at said sheath interior with the end face of the sleeve on the conduit; and,
   said second open end having internal threads.

2. The combination of claim 1 additionally comprising an outwardly directed ferrule for providing stiffness at said first open end, and for enhancing the abutting, sealing engagement of said sheath interior with the sleeve on the conduit.

3. The combination of claim 1 wherein the female connector additionally comprises an outwardly directed ferrule for providing stiffness at said first open end and for enhancing the abutting, sealing engagement of said sheath interior with the sleeve on the conduit.

4. In combination with an ultraviolet disinfection device having an alignment groove, the female connector of claim 3 wherein said ferrule also is adapted to be received in the alignment groove of the ultraviolet disinfection device.

5. In combination with first and second medical conduits, a male connector comprising:

an elongated member defining an exterior and defining an axial bore therethrough and open first and second ends;

said first open end defining a forward portion for direct telescoping engagement with the first conduit and a rearward portion of said first open end having an external threaded portion and having an annular flange; and, said second open end adapted for directly engaging the second conduit.

6. In combination with an ultraviolet disinfection device having an alignment groove, the combination of claim 5 further comprising an outwardly directed ferrule intermediate said annular flange of said first end and said second open end, said ferrule being adapted to be received in the alignment groove of the ultraviolet disinfection device.

7. A connector system comprising:
a conduit terminating in a connector end;
a sleeve fitted over said connector end of said conduit;
a female connector slidably carried on said conduit, said female connector comprising an elongated outer sheath having open first and second ends and defining an exterior and an interior, said open ends enabling said sheath to be slidably carried along said conduit, said first open end terminating in an inwardly directed lip adapted for abutting, sealing engagement at said sheath interior with said sleeve on said conduit and, said second open end having internal connecting means for cooperation with mating external connecting means;
a male connector comprising an elongated member defining an exterior and defining an axial bore therethrough and open first and second ends, said first open end defining a forward portion for telescopically engaging said sleeve on said conduit and a rearward portion of said first open end having external connecting means for cooperation with said mating internal connecting means on said female connector and having flange means adapted for abutting sealing engagement with said second end of said female connector, and said second open end of said male connector adapted for engaging a conduit.

8. The connector system of claim 7 wherein said internal connection means of said female connector comprises an internally threaded portion and wherein said external connection means of said male connector comprises an externally threaded portion.

9. The connector system of claim 8 wherein said female connector and said male connector have generally circular axial cross-sectional configurations.

10. In combination with a conduit having a sleeve attached to one end thereof, and a female device carried on the conduit and having an open end and internal threads, a male cap adapted for capping the open end of the female device comprising:
an elongated member defining an exterior and an interior and having first and second cap ends, the interior including a wall that permanently blocks flow through the interior of the member between the first and second cap ends;
said first cap end defining a forward portion for telescopically engaging the conduit sleeve and a rearward portion having external threads for cooperation with the female device internal threads; and
said second cap end having a first bore.

11. The combination of claim 10 further comprising said first cap end having an open bore that is in permanent flow separation from the bore in the cap second end and said second cap end having collar means adapted for abutting sealing engagement with the open end of the female device and enveloping a portion of the end of the female device.

12. In combination with a male device having external threads and a bore, a female cap adapted for capping the male device comprising:
an elongated sheath having first and second cap ends and defining an exterior and an interior;
said first cap end being closed and having a first lug directed from the exterior; and
said second cap end being open and having internal threads for cooperation with the male device external threads.

13. The combination of claim 12 further comprising said female cap first end having a second lug directed from said first end to the sheath interior and adapted for telescopically engaging the bore of the male device when the female cap and male device are threadingly engaged.

14. A connector closure system comprising:
a conduit terminating in a connector end;
a sleeve fitted over said connector end of said conduit;
a female connector adapted to be slidably carried on said conduit, said female connector comprising an elongated outer sheath having open first and second ends and defining an exterior and an interior, said open ends enabling said sheath to be slidable carried on said conduit, said first open end terminating in an inwardly directed lip adapted for abutting sealing engagement at said sheath interior with said sleeve on said conduit, and said second open end having internal threads for cooperation with mating external connecting means; and,
a male cap having an elongated member defining an exterior and having cap first and second ends, said cap first end defining a forward portion for telescopically engaging said sleeve on said conduit and a rearward portion having external threads for cooperation with said internal threads on said female connector, said cap second end having a first bore.

15. The connector closure system of claim 14 wherein said male cap further comprises said first cap end having an open bore and said second cap end having collar means adapted for abutting sealing engagement with the second end of the mating female connector and enveloping a portion of the second end of the mating female connector.

16. A cap connector system comprising:
a male connector comprising an elongated member defining an exterior and defining an axial bore therethrough and open first and second ends, said first open end defining a forward portion and a rearward portion having external threads and having a flange; and
a female cap adapted for capping said male connector comprising an elongated sheath having cap first and second ends and defining an extrerior and an interior, said cap first end being cosed and having a lug directed from the exterior and a lug directed from said first end to the sheath interior and adapted for engaging said first open end of said male connector, said second end being open and having internal threads for cooperation with said external threads on said male connector and said second end of said female cap adapted for abutting, sealing engagement with said flange on said male connector.

* * * * *